(12) United States Patent
Erdelmeier et al.

(10) Patent No.: US 6,525,040 B1
(45) Date of Patent: Feb. 25, 2003

(54) CYCLIC ORGANOSELENIUM COMPOUNDS, THEIR PREPARATION AND THEIR USES

(75) Inventors: Irene Erdelmeier, Paris (FR); Catherine Tailhan-Lomont, Boissise-le-Roi (FR); Marc Moutet, Bagneux (FR); Jean Chaudiere, Saint Maur des Fosses (FR); Jean-Claude Yadan, Montreuil (FR)

(73) Assignee: Oxis Isle of Man, Limited, Douglas (GB)

(*) Notice: Subject to any disclaimer, the term of this patent is extended or adjusted under 35 U.S.C. 154(b) by 0 days.

(21) Appl. No.: 09/331,736

(22) PCT Filed: Dec. 23, 1997

(86) PCT No.: PCT/EP97/07295

§ 371 (c)(1),
(2), (4) Date: May 16, 2000

(87) PCT Pub. No.: WO98/29417

PCT Pub. Date: Jul. 9, 1998

(30) Foreign Application Priority Data

Dec. 23, 1996 (FR) .............................. 96 16102

(51) Int. Cl.$^7$ .................... C07D 293/12; C07D 421/12; A61K 31/41
(52) U.S. Cl. .......................... 514/183; 514/359; 544/1; 548/121; 549/15; 549/32
(58) Field of Search ............................. 544/1; 548/121; 549/15, 32; 514/183, 359

(56) References Cited

U.S. PATENT DOCUMENTS

| 4,618,669 A | 10/1986 | Dereu et al. ................. 530/331 |
| 5,128,365 A | 7/1992 | Spector et al. ............... 514/422 |
| 5,968,920 A | 10/1999 | Erdelmeier et al. ......... 514/183 |

FOREIGN PATENT DOCUMENTS

| DE | 3027074 | 2/1982 |
| EP | 0165534 | 6/1985 |
| WO | WO95/27706 | 10/1995 |

OTHER PUBLICATIONS

Kelly, Use of antioxidants in the prevention and treatment of disease, J. Int. Fed. Clin. Chem. 10(1): 21–23, Mar. 1998 (PubMed Abstract).*
Wilson et al., 1989, J. Am. Chem. Soc. 111:5936–39.
Lambert et al., 1991, Tetrahedron, 47:9053–60.
Jacquemin et al., 1992, Tetrahedron Letters, 33:3836–66.

* cited by examiner

Primary Examiner—Deepak Rao
(74) Attorney, Agent, or Firm—Klauber & Jackson

(57) ABSTRACT

The invention is directed to novel cyclic organoselenium compounds useful as antioxidants, pharmaceutical compositions containing them, and methods for their preparation.

28 Claims, 3 Drawing Sheets

CYCLIC ORGANOSELENIUM COMPOUNDS, THEIR PREPARATION AND THEIR USES

This application is a 371 of PCT/EP97/07295 filed Dec. 23, 1997.

The principal objects of the present invention are:
novel cyclic organoselenium compounds;
the use of said novel compounds as antioxidant;
pharmaceutical compositions containing them;
a method of preparation of said novel compounds.

STATE OF THE PRIOR ART

In aerobic organisms, during the metabolism of oxygen, very reactive entities are generated whose accumulation causes deleterious effects. These organisms possess a system of regulation, composed of enzymes and small is molecules which enable controlling the production of these reactive oxygen entities. Amongst the various components of this regulation system, often called Antioxidant Defense System, glutathione peroxidases play a central role in the prevention of <<oxidative stress>> and its deleterious consequences. These antioxidant and cytoprotecting enzymes enable degrading the endogenous or exogenous cytotoxic hydroperoxides.

These enzymes catalyse the reduction of hydrogen peroxide (reaction 1) or that of organic hydroperoxides (reaction 2) by reduced glutathione (GSH):
reaction 1:

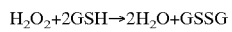

reaction 2:

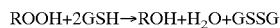

The active sites of these enzymes all contain one essential selenium atom in the form of a selenocysteine residue incorporated in the polypeptide chain.

The selenium is incorporated from selenite salts, or selenate salts, or L-seleno-methionine salts arising from food (see C. K. Chow and J. Jeng; in Selenium in Medicine and Biology, M. D. Spallholz and H. E. Ganther Eds.; (1986); Academic Press). In situations of selenium deficiency in the diet, the concentrations and activities of these glutathione peroxidases gradually decrease (see Y. X. Wang and J. Kiem.; Biological Trace Elements Res.; (1988); 15; 89 and see R. Reiter and A. Wendel; Biochem. Pharmacol.; (1983); 32; 3063–3067); this leads to an acute susceptibility to the oxidative stress (see D. B. Coursin and H. P. Cihla, Thorax, (1996), 51, 479–483). The provision of selenium in the diet is therefore a limiting factor in the biosynthesis of glutathione peroxidases.

The protecting role of glutathione peroxidases, in situations wherein the production of hydroperoxides rises, has been demonstrated following experiments of direct intracellular micro-injection of the enzyme of erythrocyte origin which have enabled demonstrating its cytoprotective effect upon the viability of fibroblasts or endothelial cells exposed to an oxidative stress (see C. to Michiels et al.; Experiment. Cell Res.; (1988); 179; 581–589). On the other hand, it has been shown that the survival of human fibroblasts is appreciably lowered when glutathione peroxidase is inhibited (see C. Michiels et al., J. Eur. Biochem., 1988, 177, 435–441).

Furthermore, the glutathione peroxidases are themselves particularly sensitive to an over-production of hydroperoxides and are rapidly inhibited under these conditions (see H. Ochi et al., Arch. of Biochem. Biophys., (1992), 294, 2, 407–411).

A certain number of pathologies such as certain ischemic cardiomyopathies for example (see J. Chaudiére, in Biologie des lipides chez l'Homme, L. Doustes-Blazy and F. Mendy eds, Edition Médicale Internationale—Paris, (1988), 137–154 and see D. Vitoux et al.; Ann. Biol. Clin.; (1996); 54; 5; 181–187) are associated with a lowering of glutathione peroxidase activity.

The demonstration of the essential role of the selenium at the active centre of these ubiquitous enzymes (see J. T. Rotruck, in Selenium in Biology and Medicine, Spallholz, J. E. Martin, J. L. Ganther H. I. eds., Avi Publishing Co, Wesport, (1981), 10–16) as well as the importance of the selenium in the regulation of oxidative damages generated during certain pathologies (see Cadenas, E. and Sies, H., Adv. Enz. Regul., (1985), 23, 217–237 and see Ursini, F., Bindoli, A., Chem. Phys. Lipids, (1987), 44, 255–276) has enabled the emergence of a novel class of organoselenium compounds as potential drugs.

Two types of compounds have been designed and prepared to this end.

On one side, modified macromolecules possessing a selenium atom introduced chemically such as selenosubtilisin (see Z. P. Wu and D. Hilvert, J. Am. Chem. Soc., (1990), 112, 5647–5648) or even a seleno-abzyme (see G. M. Luo et al., Biochem. Biophys. Res. Comm., 1994, 198, 3, 1240–1247). However, the use of proteins with a therapeutic aim is difficult to envisage for the following reasons:
their biostability is often insufficient;
an efficient method for ensuring their intra-cellular targeting does not exist;
they cannot be administered orally.

On the other side, synthetic molecules of low molecular weight have been synthetized, of which 2-phenyl-1,2-benzisoselenazolin-3-one (ebselen) (see H. Sies, Free Rad. Biol. Med., (1993), 14, 313–323) was the first compound described as having a glutathione peroxidase activity. Homologs of said ebselen, i.e. 2H-3,4-dihydro-1,2-benzoselenazin-3-ones, have also been described by Pierre V. Jacquemin et al. in Tetrahedron Letters, (1992), Vol. 33, No. 27, 3863–3866. In fact, several organoselenium derivatives have been described as glutathione peroxidase mimics, i. e. capable of reducing hydroperoxides in the presence of a biological thiol such as glutathione or lipoic acid (see I. A. Cotgreave et al., Biochem. Pharmacol., (1992), 43, 793–802 and C. M. Andersson et al., Free Rad. Biol. Med., (1994), 16, 17–28 and S. R. Wilson et al., J. Am. Chem. Soc., (1989), 111, 5936–5939 and V. Galet et al., J. Med. Chem., (1994), 37, 2903–2911). The patent application WO-A-95/27706 describes compounds of benzisoselenazoline and benzisoselenazine structure having a glutathione peroxidase activity inter alia.

These organoselenium compounds, which are mimics of glutathione peroxidase, invariably produce catalytic intermediates of the selenol and/or diselenide type.

Amongst these, 2-phenyl-1,2-benzisoselenazolin-3-one (ebselen) and some of its derivatives do not seem to have any major toxic effect (see A. Wendel et al.; Biochem. Pharmacol.; (1984); 33; 3241–3245 and S. D. Mercurio and G. F. Combs; Biochem. Pharmacol.; (1986); 35; 4505–4509). 2-Phenyl-1,2-benzisoselenazolin-3-one (ebselen) is however very little soluble in water, even in the presence of an excess of glutathione GSH, which limits its pharmacological applications.

The biochemical and pharmacological properties of the organoselenium compounds which have been synthesised and studied have been recently reviewed (see M. J. Pamham and E. Graf; Progress in Drug Res.; (1991); 36; 9–47 and M. J. Pamham, Exp. Opin. Invest. Drugs, (1996), 5, 7, 861–570).

One of the aims of the present invention is to design organoselenium compounds having a catalytic activity of the glutathione peroxidase type in the presence of physiological concentrations of glutathione GSH.

These compounds must be able to penetrate the target tissues or cells, be soluble in water at active concentrations and must not efficiently reduce oxygen into toxic by-products.

These aims are attained by virtue of the present invention which resides on the design of cyclic organoselenium compounds whose antioxidant and cytoprotecting activities have been demonstrated by the Applicant and which are given below.

DESCRIPTION OF THE INVENTION

The aim of the present invention is:
1) to solve the novel technical problem consisting of providing novel cyclic heteroaryl selenium compounds having a very good antioxidant and cytoprotecting activity, thus constituting valuable active principles of pharmaceutical compositions;
2) to solve the novel technical problem above according to a solution which includes a method of preparation of these novel compounds which is easy to carry out.

The technical problems set forth above are solved for the first time in a simultaneous manner by the present invention in a simple way; the method of preparation of said novel compounds being relatively easy to carry out and giving good yields.

According to its first aspect, the present invention thus relates to novel cyclic organoselenium compounds, having the general formula (I) below:

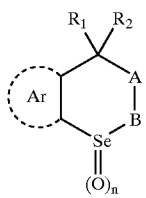

(I)

in which:
R$_1$=hydrogen; lower alkyl; optionally substituted aryl; optionally substituted lower aralkyl;
R$_2$=hydrogen; lower alkyl; optionally substituted aryl; optionally substituted lower aralkyl;
A=CO; (CR$_3$R$_4$)$_m$;
B=NR$_5$; O; S;
Ar=optionally substituted phenyl or an optionally substituted radical of formula:

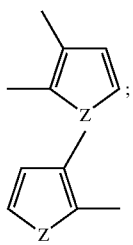 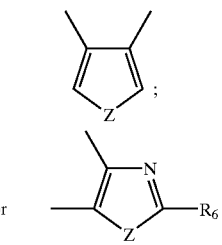

in which:
Z=O; S; NR$_5$;
R$_3$=hydrogen; lower alkyl; optionally substituted aryl; optionally substituted lower aralkyl R$_4$=hydrogen; lower alkyl; optionally substituted aryl; optionally substituted lower aralkyl;
R$_5$=hydrogen; lower alkyl; optionally substituted aryl; optionally substituted lower aralkyl; optionally substituted heteroaryl; optionally substituted lower heteroaralkyl; CO(lower alkyl); CO(aryl); SO$_2$ (lower alkyl); SO$_2$(aryl);
R$_6$=hydrogen; lower alkyl; optionally substituted aryl; optionally substituted lower aralkyl; optionally substituted heteroaryl; optionally substituted lower heteroaralkyl; trifluoromethyl;

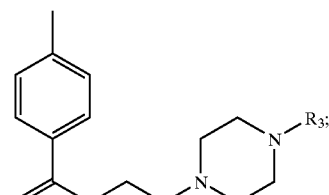

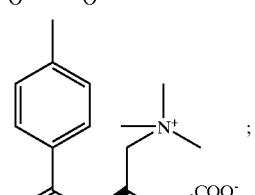

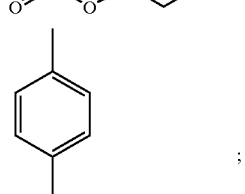

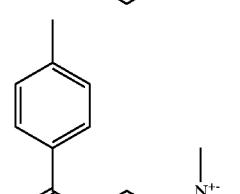

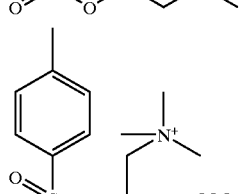

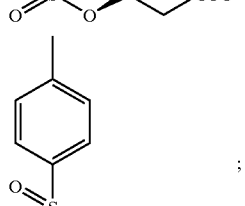

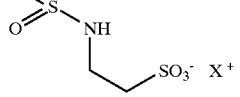

-continued

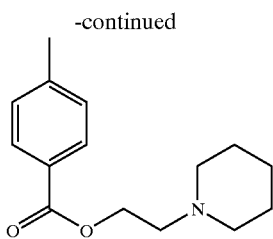

m=0 or 1;
n=0 or 1;
X⁺ represents the cation of a pharmaceutically acceptable base; and their pharmaceutically acceptable salts of acids or bases with the proviso that:
when B=NR₅ with R₅ hydrogen, lower alkyl, optionally substituted lower aralkyl, CO(lower alkyl), and A=CO or (—CH₂—)$_m$, then Ar is different from an optionally substituted phenyl.

Said general formula (I) more particularly encompasses the four compounds, preparation of which is illustrated in the examples joined to this specification.

Said general formula (I) includes every stereoisomer, epimer and diastereoisomer, as a mixture or in isolated form.

It also includes, as indicated, the salts of pharmaceutically acceptable acids or bases of said compounds of formula (I).

Amongst the pharmaceutically acceptable acids, hydrochloric, hydrobromic, hydroiodic, sulphuric, tartaric, methanesulphonic, trifluoromethane-sulphonic acid, . . . can be cited in a non-limiting way.

Amongst the pharmaceutically acceptable bases, sodium hydroxide, potassium hydroxide, alkali metal or alkaline earth metal carbonates, or organic bases such as triethylamine or arginine, . . . can be cited in a non-limiting way.

Within the context of the present description and annexed claims:
the terms "lower alkyl and lower alkoxy (see below)" are understood as meaning straight or branched alkyl and alkoxy groups having from 1 to 8 carbon atoms;
the term "aryl" is understood as meaning an aromatic group selected from phenyl and naphthyl groups;
the term "heteroaryl" is understood as meaning a mono- or bicyclic aromatic group, each cycle, or ring, comprising five or six atoms and said cycle, or ring, or both cycles, or rings, including in its carbon skeleton from one to three heteroatoms selected from nitrogen, oxygen and sulphur;
the terms "lower aralkyl" and "lower heteroaralkyl" are understood as meaning, in view of the definitions above, phenyl($C_1$–$C_8$)alkyl or naphthyl($C_1$–$C_8$)alkyl and heteroar($C_1$–$C_8$)alkyl respectively;
the terms "substituted" concerning the terms aryl, aralkyl, phenyl, radical (five-membered, including Z), heteroaryl, heteroaralkyl, as defined above, signifies that the groups in question are substituted on the aromatic part with one or more identical or different groups selected from the groups : ($C_1$–$C_8$)alkyl, trifluoromethyl, ($C_1$–$C_8$)alkoxy, hydroxy, nitro, amino, ($C_1$–$C_8$)alkylamino, di($C_1$–$C_8$)alkylamino, sulphoxyl, sulphonyl, sulphonamide, sulpho($C_1$–$C_8$)alkyl, carboxyl, carbalkoxyl, carbamide (it being possible for said ($C_1$–$C_8$)alkyl groups to be linear or branched) or substituted with one or more halogen atoms.

Finally, when R₅ represents a hydrogen atom (B=—NH), the invention also includes the salts obtained with the pharmaceutically acceptable acids.

Said novel compounds have proved to be, as specified above, excellent antioxidant agents, the use of which is recommended by the Applicant in various fields. This use of said novel cyclic organoselenium compounds of the invention—compounds having formula (I) as defined above—as antioxidant agents, constitutes the second aspect of said invention.

Within the context of this second aspect, the use of said compounds of formula (I), is more particularly claimed as antioxidant agents:
intended to be added to preserving media of grafts for transplantation of organs of human or animal origin such as the heart, the liver, the kidney and the lungs; and
intended for (as active principle) the manufacture of pharmaceutical compositions with antioxidant activity, suitable especially:
for treatments of any physiopathological condition in which an over-production of cytotoxic hydroperoxides contributes to the functional impairments of cells or tissues; and more particularly including:
the treatment of inflammatory and/or ischemic cardio- and cerebro-vascular pathologies, such as the preventive and/or curative treatment of arterial restenoses following an angioplasty, the preventive and/or curative treatment of arterial stenoses following artery allografts, the treatment of intermittent claudication in patients affected with obstructive ischemia of the lower members, the treatment of cerebro-vascular accidents of ischemic origin;
the treatment of inflammatory and/or ischemic digestive pathologies, such as the treatment of acute inflammations of the bowel (Crohn's disease, hemorrhagic rectocolitis);
the treatment of inflammatory and/or ischemic respiratory pathologies, such as the treatment of adult respiratory distress syndrome (ARDS) and infant respiratory distress syndrome (IRDS);
the treatment of inflammatory and/or ischemic ophthalmic pathologies, such as the treatment of glaucoma;
the treatment of cataracts;
the treatment of acute ophthalmic allergies
the treatment of impairments of the retina which are associated with a macular degeneration;
the treatment of viral infections causing an immunodeficiency, such as the treatment of AIDS;
the treatment of post-radiotherapy fibroses.

Generally, the potential therapeutic applications of the compounds of the invention include the treatment of any physiopathological condition in which an over-production of cytotoxic hydroperoxides contributes to the functional impairments of cells or tissues. Such an over-production of hydroperoxides can be endogenous and secondary to the activation of the intra-cellular metabolic pathways such as, for example, those of the flavine or cytochrome P-450 oxygenases, those of the lipoxygenases, those of the monoamine oxidases. The over-production can also be due to the activation of the endothelial cells (xanthine oxidase, 15-lipoxygenase), or of blood platelets (cyclooxygenase and 12-lipoxygenase). It can also be due to the activation, by cytokines such as TNF-α for example, of inflammatory and/or immune cells such as neutrophils, macrophages or lymphocytes for example. It may also be due to an intoxication by a free-radical generating xenobiotic. Finally, it may be due to a voluntary irradiation such as practised during a radiotherapy, or an accidental irradiation.

More particularly, the second aspect of the present invention includes the use of compounds of the invention for the manufacture of pharmaceutical compositions intended for the treatment:

- of inflammatory diseases of the bowel such as Crohn's disease or hemorrhagic rectocolitis;
- of adult respiratory distress syndrome and infant respiratory distress syndrome;
- of cataracts;
- of AIDS;
- of post-radiotherapy fibroses.

From the second aspect of the present invention—use of the novel compounds de formula (I) as antioxidant agents—, such as described above, comes the third aspect which is dealt with now, namely the pharmaceutical compositions containing said compounds of formula (I) as active principle.

Thus, according to its third aspect, the present invention relates to pharmaceutical compositions, notably having an antioxidant activity, and comprising at least one cyclic organoselenium compound of the general formula (I), or one of its pharmaceutically acceptable salts of an acid or a base, as active ingredient, optionally incorporated in a pharmaceutically acceptable excipient, carrier or vehicle.

Said pharmaceutical compositions of the invention, according to an advantageous embodiment, contain said active ingredient in an amount between 0.1 and 5% by weight, advantageously between 0.1 and 1% by weight based on their total weight. According to another advantageous embodiment, said compositions are in the form of unit doses comprising from 1 to 500 mg of at least one cyclic organoselenium compound of the invention (optionally incorporated in a pharmaceutically acceptable excipient, carrier or vehicle).

The pharmaceutical compositions of the invention can be formulated for, or intended for, oral, rectal or topical administration, (the compounds of formula (I) may especially be formulated for ophthalmic applications in the form of an eye lotion) or even as intra-ventricular, intramuscular, subcutaneous or intravenous injections.

The pharmaceutically acceptable excipients, vehicles and carriers which can be included in their formulation are products which are well-known to the person skilled in the art and are not described in detail here.

The pharmaceutical compositions of the invention which contain the antioxidant agents disclosed by the present invention (compounds of formula (I)) are especially suitable for the treatment of any physiopathological condition in which an over-production of cytotoxic hydroperoxides contributes to the functional impairments of cells or tissues; it being possible for said over-production of hydroperoxides to be due to any one of the causes presented above in the present description, with reference to the second aspect of the invention (activation of the intra-cellular metabolic pathways, enzyme activation, macrophage or lymphocyte activation, intoxication by a free-radical generating xenobiotic, voluntary or accidental irradiation).

More specifically, said pharmaceutical compositions are suitable for the treatment of the pathologies listed above in the present description (with reference to the second aspect of the invention).

It is hereby specified that the antioxidant and therapeutical or pharmacological activities of the cyclic organoselenium compounds of the general formula (I) above have been demonstrated according to safe and reliable tests well-known to the person skilled in the art, which comprise:

- a/ measuring the glutathione peroxidase activity;
- b/ measuring the cytoprotective effect in human umbilical vein endothelial cells.

It is hereby incidentally mentioned that the preparation of pharmaceutical compositions incorporating an effective amount of at least one organoselenium compound of formula (I) according to the invention as well as the therapeutical treatments implying the use of such a compound make up an integral part of the present invention.

According to its last aspect, given below, the invention even relates to a method of preparation of said organoselenium compounds of formula (I). Said method comprises the following essential steps:

- a/ preparing or using an orthohalo(hetero)arylacetonitrile derivative, optionally mono- or gem- disubstituted in the benzylic position; then, according to the series considered:

for the preparation of said compounds of formula (I) in which $A=(CR_3R_4)_m$ with m=0 (A does not exist) and n=0:
  - b1/ hydrolyzing said nitrile derivative into an amide derivative,
  - c1-1/ transforming this amide derivative into an amine derivative by a transposition reaction according to conventional methods,
  - d1-1/ allowing said amine derivative to react with a nucleophilic selenium derivative, optionally generated in situ, in the presence of a copper Cu(I) salt, in a polar organic solvent, to lead to the corresponding (hetero)arylisoselenazoline derivative,
  - e1-1/ optionally, N-alkylating or N-arylating or N-acylating or N-sulphonylating, according to conventional procedures, said (hetero)arylisoselen-azoline derivative;

for the preparation of said compounds of formula (I) in which A=CO and n=0:
  - b1/ hydrolyzing said nitrile derivative into an amide derivative,
  - c1-2/ allowing said amide derivative to react with a nucleophilic selenium derivative, optionally generated in situ, in the presence of a copper Cu(I) salt, in a polar organic solvent, to lead to the corresponding (hetero)arylisoselen-azone derivative,
  - d1-2/ optionally, N-alkylating or N-arylating or N-acylating or N-sulphonylating, said (hetero) arylisoselenazone derivative;

for the preparation of said compounds of formula (I) in which $A=CH_2$ and n=0:
  - b2/ reducing said nitrile derivative into an amine derivative with the aid of borane for example in an ethereal solvent such as tetrahydrofuran for example,
  - c2/ allowing said amine derivative to react with a nucleophilic selenium derivative, optionally generated in situ, in the presence of a copper Cu(I) salt, in a polar organic solvent, to lead to the corresponding (hetero)arylisoselenazine derivative,
  - d2/ optionally, N-alkylating or N-arylating or N-acylating or N-sulphonylating, according to conventional procedures, said (hetero)arylisoselenazine derivative;

for the preparation of said compounds of formula (I) in which $A=(CR_3R_4)$ ($\neq CH_2$) and n=0:
  - b3/ carrying out a mono- or a bis-C-alkylation of said nitrile derivative according to conventional methods, with the aid of an organolithium derivative for example, in an ethereal solvent such as tetrahydrofuran;

c3/ allowing the amine derivative obtained to react with a nucleophilic selenium derivative, optionally generated in situ, in the presence of a copper Cu(I) salt, in a polar organic solvent, to lead to the corresponding (hetero)arylisoselenazine derivative;

d3/ optionally, N-alkylating or N-arylating or N-acylating or N-sulphonylating, according to conventional procedures, said corresponding (hetero)arylisoselenazine derivative;

finally, optionally, for the preparation of compounds of formula (I) in which n=1, Se-oxidising, according to conventional procedures, the corresponding derivative of formula (I) (wherein n=0) obtained previously according to any one of the synthetic routes above.

Said method is close to that described in the application WO-A-95/27706. In a way, it constitutes an adaptation of said method according to WO-A-95/127706 for obtaining heteroaromatic derivatives. The implementation of each of its steps does not give rise to any particular difficulty to the person skilled in the art.

According to the advantageous variants of implementation of said method:

the nucleophilic selenium derivative (which intervenes in steps d1-1/, c1-2/, c2/ and c3/g) is a selenocyanate salt, such as potassium selenocyanate for example, which can be:
  either generated in situ from selenium metal Se(0) and a cyanide salt, such as potassium cyanide for example,
  or added to the reaction medium as such;

the copper salt Cu(I) (which intervenes in the same steps) is cuprous iodide;

the polar organic salt (which intervenes in the same steps) is dimethylformamide;

the intervening oxidant for the Se-oxidation is either peracid, such as meta-chloroperbenzoic acid or hydrogen peroxide.

Other aims, characteristics and advantages of the invention will appear clearly in the light of the following explanatory description made with reference to various non-limiting examples given solely as illustration and which in no way limit the scope of the invention. In the examples, all percentages are given by weight unless otherwise indicated.

BRIEF DESCRIPTIONS OF THE FIGURES

EXPERIMENTAL SECTION

I Synthesis

Figure 1:
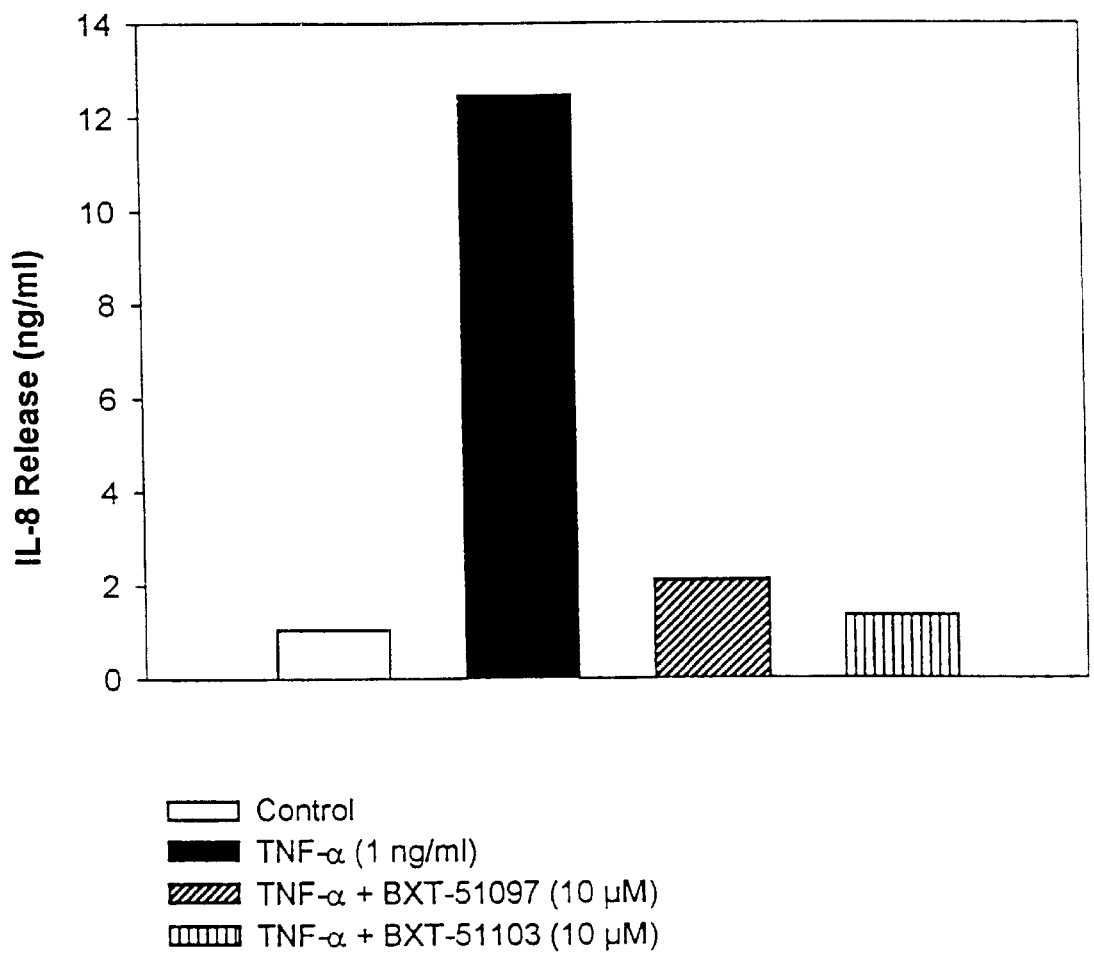
FIG. 1 shows the inhibition of the TNF-α-induced interleukin 8 release by endothelial cells (HUVEC).

All reactions were carried out under an inert nitrogen atmosphere unless otherwise indicated.

Mass spectra were recorded on a Nermag R10-10B instrument. Ionisation used is either electron impact (EI) at 70 electron-volts or chemical ionisation (CI) in ammonia or isobutene, or fast atom bombardment (FAB) on a glycerol matrix.

The $^1$H and C$^{13}$C NMR spectra were recorded on a Varian Gemini-200 instrument, the $^{77}$Se NMR spectra on a Bruker AMX 500 instrument. The chemical shifts are given in ppm with respect to tetramethylsilane ($^1$H and $^{13}$C NMR spectra) or to dimethylselenide ($^{77}$Se NMR spectra). The multiplicities are expressed as follows: "s" for singlet, "bs" for broad singlet, "d" for doublet, "t" for triplet, "q" for quadruplet and "m" for multiplet; "E" for even and "O" for odd.

The melting points (m.p. 0° C.) were recorded on a Gallenkamp instrument and are given uncorrected.

Purification by liquid column chromatography was carried out with Merck® Si60F$_{254}$.

EXAMPLE 1

Preparation of 4,4-Dimethyl-thieno-[3,2-e]-isoselenazine:

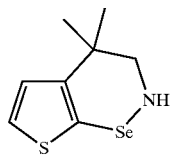

BXT 51097

A/ Preparation of 2-Bromo-3-bromomethyl-thiophene:

This compound is prepared from 2-bromo-3-methyl-thiophene (1.85 g; 10.4 mmoles) according to a method identical to that described in the literature by E. Campaigne and W. M. Lesuer (J. Am. Chem. Soc., 1949, 71 333–335), and is obtained as a colourless oil (2.45 g). The product is used as such in the next step.

Yield: 95%; Physical characteristics: * NMR $^1$H: (CDCl$_3$); 4.43 ppm (s, 2H); 6.98 ppm (d, 1H, J=5.7 Hz); 7.24 ppm (d, 1H, J=5.7 Hz).

B/ Preparation of 3-(2-Bromo)-thienyl-acetonitrile:

A round-bottomed flask containing the preceding bromo derivative (2.10 g ; 8.2 mmoles) dissolved in methanol (8 ml), is cooled in a water bath. Under an inert atmosphere, sodium cyanide (0.610 g; 12.3 mmoles) is added all at once. The mixture is left for 4 hours at ambient temperature. The solvent is evaporated under reduced pressure. The residue is taken up into 15 ml of water and extracted with 2×15 ml of dichloromethane. The organic phases are combined, washed with water and then with a saturated solution of sodium chloride, dried over magnesium sulphate and then filtered. After evaporation of the solvent and silica gel chromatography (eluent gradient: pure cyclohexane, then cyclohexane/ethyl acetate (90/10)), the desired product is obtained as a pale yellow oil (1.05 g).

Yield: 64%; Physical characteristics: * NMR$^1$H: (CDCl$_3$); 3.64 ppm (s, 2H); 7.01 ppm (d. 1H, J=5.8 Hz); 7.31 ppm (d, 1H, J=5.8 Hz). * NMR$^{13}$C: (CDCl$_3$); 18.62 ppm (E); 112.28 ppm (E); 117.12 ppm (E); 127.50 ppm (O); 128.03 ppm (O); 129.80 ppm (E). * MS: (EI; 70 eV); 203/201 (M$^{+\cdot}$; 45); 122 (M—Br; 100); 98 (60).

C/ Preparation of 2-[3'-(2'-Bromo)-thienyl]-2-methyl-propionitrile:

To a suspension of NaH (0.140 g; 4 mmoles) in anhydrous DMF (1 ml), kept at −10° C. under an inert atmosphere is added slowly (~5–10 minutes), a solution containing the preceding derivative (0.202 g; 1 mmole) and methyl iodide (0.570 g, 4 mmoles) in anhydrous DMF (1.5 ml). The reaction mixture is stirred at 0° C. for one hour, then at ambient temperature for about 2 hours. The residue is taken up into 10 ml of water and extracted with 2×10 ml of ethyl acetate. The organic phases are combined, washed with 3×10 ml of water and then with a saturated solution of sodium chloride, dried over magnesium sulphate and then filtered. The desired product is obtained, after evaporation of the solvent, as a yellow brown oil (0.240 g). It will be used as such in the next step.

Yield: ~quantitative; Physical characteristics: * NMR$^1$H: (CDCl$_3$); 1.80 ppm (s, 6H); 6.94 ppm (d, 1H, J=5.9 Hz); 7.24 ppm (d, 1H, J=5.9 Hz). * NMR$^{13}$C: (CDCl$_3$) 27.35 ppm; 33.68 ppm; 109.74 ppm; 122.97 ppm; 126.39 ppm; 126.54 ppm; 138.32 ppm. * MS: (EI; 70 eV); 231/229 (M$^{+•}$; 30); 216/214 (M-15; 70); 153/151 (M—Br; 45); 125/123 (42); 97 (100).

D/ Preparation of 2-[3'-(2'-Bromo)-thienyl]-2-methyl-propylamine:

The derivative prepared in Example 1/C, (0.230 g; 1 mmole) is dissolved in anhydrous THF (1 ml), under nitrogen. A solution of aluminium hydride AlH$_3$ in anhydrous THF (1.5 M; 1.0 ml; 1.5 mmoles) is added slowly to the reaction mixture at ambient temperature. The mixture is refluxed for 2 hours. Brought back to ambient temperature, the medium is first of all hydrolysed with 1 to 2 ml of water and then with 2 ml of a 2N solution of HCl. After the evaporation of the solvents, the residue is taken up into 5 ml of a 2N solution of HCl and extracted with 3×10 ml of TBME. The aqueous phase is made alkaline (pH=12), and then extracted with 3×6 ml of ethyl acetate. The organic phases are combined, washed with 2×10 ml of water and then with a saturated solution of sodium chloride, dried over magnesium sulphate and then filtered. The desired product is obtained after evaporation of the solvent as a yellow oil (0.125 g).

Yield: 53%; Physical characteristics: * NMR$^1$H: (CDCl$_3$); 1.12 ppm (bs, —NH2); 1.38 ppm (s, 6H); 2.98 ppm (s, 2H); 6.84 ppm (d, 1H, J=5.8 Hz); 7.16 ppm (d, 1H, J=5.8 Hz). * NMR$^{13}$C: (CDCl$_3$); 26.38 ppm; 40.15 ppm; 52.19 ppm; 107.04 ppm; 125.61 ppm; 129.36 ppm; 145.17 ppm. * MS: (CI; isobutane); 236/234 (MH+; 100); 220/218 (M—NH2; 5); 154 (M—Br; 47); 125/123 (12).

E/ Preparation of 4,4-Dimethyl-thieno-[3,2-e]-isoselenazine:

To a solution of potassium selenocyanate (1.0 g ; 6.9 mmoles) in anhydrous DMF (7 ml), is added the derivative prepared as in Example 1/D (0.702 g; 3 mmoles). To this solution cooled to 5° C. and under an inert atmosphere are then added copper (I) iodide (0.570 g; 3 mmoles), then triethylamine (0.900 g; 9 mmoles). The reaction mixture rapidly becomes deeply coloured and is then kept stirred for 17 hours at ambient temperature and under nitrogen. 70 ml of an aqueous sodium cyanide solution (0.560 g ; 11.4 mmoles) are added so as to complex the copper iodide out and to thus facilitate the separation of the two phases. After decanting, the aqueous phase is extracted with 70 ml of ethyl acetate. The organic phase is washed with 5×50 ml of water and then with 2×50 ml of a saturated solution of sodium chloride, dried over magnesium sulphate, and then filtered. The desired product is obtained after evaporation of the solvent and silica gel column chromatography (eluent: cyclohexane/ethyl acetate (95/5)) as bright yellow crystals (0.390 g).

Yield: 56%; Physical characteristics: * m.p. ° C.: 51.6–51.8 ° C. (hexane/ethyl acetate: 75/1); * NMR$^1$H: (CDCl$_3$); 1.21 ppm (s, 6H); 3.18 ppm (s, 2H); 3.29 ppm (bs, —NH); 7.05 ppm (d, 1H, J=5.2 Hz); 7.27 ppm (d, 1H, J=5.2 Hz). * NMR$^{13}$C: (CDCl$_3$); 28.63 ppm (O); 33.69 ppm (E); 61.50 ppm (E); 119.78 ppm (E); 123.93 ppm (O); 127.18 ppm (O); 141.84 ppm (E). * NMR$^{77}$Se: (CDCl$_3$) 737.0 ppm. * MS: (EI; 70 eV); 233 (M$^{+•}$; 82); 204 (79); 189 (100); 124 (22); 97 (17).

EXAMPLE 2

Preparation of 4,4-Dimethyl-thieno-[3,2-e]-isoselenazine-1-oxide:

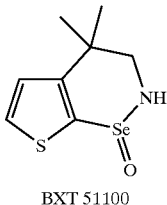

BXT 51100

The 4,4-dimethyl-thieno-[3,2-e]-isoselenazine derivative, BXT 51097, (0.115 g; 0.5 mmoles) (see Example 1) is dissolved at ambient temperature in methanol (3 ml) with stirring. After adding 5% hydrogen peroxide (0.3 ml; 0.52 mmoles), the stirring is kept up for 3 hours. The solvent is evaporated under reduced pressure. The residue is taken up into 15 ml of dichloromethane and washed with 3×5 ml of a saturated solution of sodium chloride, dried over magnesium sulfate, and then filtered. The desired product is obtained after evaporation of the solvent as white crystals (0.065 g).

Yield: 52%; Physical characteristics: * m.p. ° C.: 89–90° C.; * NMR$^1$H: (CDCl$_3$); 1.27 ppm (s, 3H); 1.33 ppm (s, 3H); 2.80 ppm (d, 1H, J=13 Hz); 3.86 ppm (d, 1H, J=13 Hz); 7.13 ppm (d, 1H, J=5.4 Hz); 7.54 ppm (d, 1H, J=5.4 Hz). * NMR$^{13}$C: (CH$_3$SeCH$_3$). 26.82 ppm (O); 27.12 ppm (O); 35.20 ppm (E); 46.89 ppm (E); 125.96 ppm (O); 129.90 ppm (O); 131.24 ppm (E); 149.44 ppm (E). * NMR$^{77}$Se: (CH$_3$SeCH$_3$); 996.4 ppm. * MS: (FAB+; para-nitrobenzyl alcohol); 250 (MH+; 40); 123 (22); 95 (50).

EXAMPLE 3

Preparation of 4,4-Dimethyl-thieno-[2,3-e]-isoselenazine:

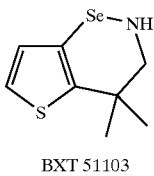

BXT 51103

A/Preparation of 3-Bromo-2-hydroxymethyl-thiophene:

2-(3-Bromothienyl)carboxylic acid (7 g; 34 mmoles) is dissolved in 25 ml of anhydrous THF. A solution of aluminium hydride AlH$_3$ in anhydrous THF (2 M; 42 ml; 84 mmoles) is added slowly at a temperature of 0° C. At the end of the addition, the reaction mixture is refluxed for 3 hours. After cooling to 0° C., water (200 ml) and hydrochloric acid (1N, 150 ml) are added. The mixture is decanted and the aqueous phase extracted with 3×150 ml of tert-butyl methyl ether. The organic phases are combined and then washed with 150 ml of a saturated solution of sodium chloride, dried over magnesium sulphate and filtered. The solvent is evaporated under reduced pressure. The desired product is obtained as a brown oil and is used as such in the next step.

Yield: 95%; Physical characteristics: * NMR$^1$H: (CD$_3$OD) 4.69 ppm (s; 2H); 6.95 ppm (d; 1H, J=5.2 Hz); 7.39 ppm (d; 1H, J=5.2 Hz). * NMR$^{13}$C: (DMSO-d$_6$) 57.80 ppm; 106.28 ppm; 126.11 ppm; 129.80 ppm; 141.15 ppm. * MS: (EI, 70 eV); 194/192 (M$^{+•}$; 80%); 177/175 (30%); 113 (50%); 98 (60%); 85 (100%).

B/Preparation of 3-Bromo-2-chloromethyl-thiophene

The preceding derivative (6.2 g; 32 mmoles) is dissolved in anhydrous dichloromethane (180 ml). Thionyl chloride (5.7 g; 3.5 ml; 48 mmoles) is added slowly, the stirring is then kept up for 18 hours at ambient temperature. The reaction mixture is poured into 200 ml of water and then decanted. The aqueous phase is extracted with 2×100 ml of tert-butyl methyl ether. The organic phases are combined, washed with a saturated solution of sodium bicarbonate (200 ml), dried over magnesium sulphate and filtered. The solvent is evaporated under reduced pressure. The desired product is obtained as a brown oil and is used as such for the next step.

Yield: 90% Physical characteristics: * NMR$^1$H: (CDCl$_3$); 4.75 ppm (s; 2H); 6.95 ppm (d; 1H, J=5.2 Hz); 7.30 ppm (d; 1H, J=5.2 Hz). * NMR $^{13}$C: (CDCl$_3$); 39.5 ppm; 112.5 ppm; 127.5 ppm; 131.0 ppm; 135.0 ppm. * MS: (EI, 70 eV); 212 (M$^{+•}$; 35%); 177(100%); 96 (20%).

C/ Preparation of 2-(3-Bromo)-thienyl-acetonitrile:

The preceding derivative (6 g; 28 mmoles) is dissolved in DMSO (100 ml). Sodium cyanide (2 g; 41 mmoles) is added and stirring is kept up for 2 hours. The reaction mixture is poured into 200 ml of water. The mixture is extracted with 3×100 ml of tert-butyl methyl ether and then 2×100 ml of dichloromethane. The organic phases are combined, washed with 3×200 ml of water, dried over magnesium sulphate and filtered. The solvent is evaporated under reduced pressure. The residue is taken up into 400 ml of cyclohexane and washed with 4×100 ml of water. The organic phase is dried over magnesium sulphate and filtered. The solvent is evaporated off under reduced pressure. The desired product is obtained as a colourless oil after distillation of the residue in a Küigelrohr distillation apparatus (T=200° C., p=0.1 mbar).

Yield: 60%; Physical characteristics: * NMR$^1$H: (CDCl$_3$) 3.84 ppm (s; 2H); 7.00 ppm (d; 1H, J=5.2 Hz); 7.31 ppm (d; 1H, J=5.2 Hz). * NMR$^{13}$C: (CDCl$_3$); 18.39 ppm; 112.29 ppm; 116.30 ppm; 126.37 ppm; 126.65 ppm; 130.92 ppm. * MS: (EI, 70 eV); 203/201 (M$^{+•}$; 29%); 122 (100%); 98 (40%).

D/Preparation of 2-[2'-(3'-Bromo-thienyl)]-2-methyl-propionitrile:

This compound is obtained according to a procedure very similar to that of Example 1/C from the preceding derivative in the form of a yellow oil.

Yield: 90%; Physical characteristics:
* NMR$^1$H: (acetone-d$_6$); 1.77 ppm (s; 6H); 7.02 ppm (d; 1H, J=5.2 Hz); 7.44 ppm (d; 1H, J=5.2 Hz). * NMR$^{13}$C: (CDCl$_3$); 20.11 ppm; 33.90 ppm; 109.68 ppm; 122.15 ppm; 124.39 ppm; 133.21 ppm; 137.27 ppm. * MS: (EI, 70 eV); 231/229 (M$^{+•}$; 50%); 2161214 (100%); 189/187 (45%).

E/Preparation of 2-[2'-(3'-Bromo-thienyl)]-2-methyl-propylamine:

This compound is obtained according to a method very similar to that of Example 1/D from the preceding derivative as a pale yellow oil.

Yield: 80%; Physical characteristics: * NMR$^1$H: (CDCl$_3$); 1.10 ppm (bs; 2H); 1.44 ppm (s; 6H); 3.06 ppm (s; 2H); 6.93 ppm (d; 1H, J=5.2 Hz); 7.07 ppm (d; 1H, J=5.2 Hz). * NMR$^{13}$C: (CDCl$_3$); 26.45 ppm; 40.76 ppm; 51.78 ppm; 105.89 ppm; 123.01 ppm; 133.26 ppm; 145.00 ppm. * MS: (CI, isobutane); 236/234 (MH$^+$; 40%); 154 (25%); 93 (100%).

F/Preparation of 4,4-Dimethyl-thieno-[2,3-e]-isoselenazine: BXT 51103

This compound is obtained according to a method very similar to that of Example 1/E from the preceding derivative as a yellow oil crystallising at −20° C.

Yield: 54%; Physical characteristics: * m.p. ° C.: 31° C.; * NMR$^1$H: (CDCl$_3$); 1.33 ppm (s; 6H); 3.20 ppm (s; 2H); 3.30 ppm (bs; 1H); 6.68 ppm (d; 1H, J=5.3 Hz); 7.24 ppm (d; 1H, J=5.3 Hz). * NMR$^{13}$C: (CDCl$_3$); 30.02 ppm; 34.16 ppm; 61.35 ppm; 119.64 ppm; 122.89 ppm; 124.57 ppm; 139.89 ppm. * NMR$^{77}$Se: (CH$_3$SeCH$_3$); 727.0 ppm. * MS: (EI, 70 eV); 233 (M$^{+•}$; 86%); 203 (10%); 189 (40%); 153 (20%), 124 (40%); 77 (35).

EXAMPLE 4

Preparation of 4,4-Dimethyl-thieno-[23-e]-isoselenazine-1-oxide:

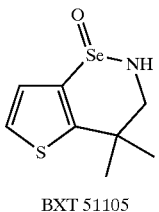

BXT 51105

This compound is obtained according to a method very similar to that of Example 2 from the preceding derivative (BXT 51103: see Example 3) as a colourless oil.

Yield: quantitative; Physical characteristics: * NMR $^1$H: (CDCl$_3$); 1.33 ppm (s; 3H); 1.38 ppm (s; 3H); 2.82 ppm (d; 1H, J=13 Hz); 3.78 ppm (d; 1H, J=13 Hz); 4.90 ppm (bs; 1H); 7.09 ppm (d; 1H, J=5.4 Hz); 7.26 ppm (d; 1H, J=5.4 Hz). * NMR$^{13}$C: (CDCl$_3$); 29.29 ppm; 29.45 ppm; 36.28 ppm; 48.03 ppm; 124.68 ppm; 126.03 ppm; 131. 52 ppm; 153.94 ppm. * NMR$^{77}$Se: (CH$_3$SeCH$_3$); 988.20 ppm. * MS: (CI; isobutane); 250 (MH$^+$; 40%); 234 (100%); 93 (40%).

II/Activities

EXAMPLE 5

Measurement of the Glutathione Peroxidase Activity of Compounds of General Formula I The glutathione peroxidase activity is determined by using a 50 mM HEPES buffer, pH=7.3 (at 37° C.), containing 0.2 mM DTPA, 0.144 mM NADPH, 2.2 mM reduced glutathione (GSH) and 1.1 U/ml glutathione disulphide reductase. This buffer further contains 110 U/ml catalase when hydrogen peroxide is not used as substrate.

To 1.5 ml of the buffer described above, are added 100 μl of an ethanolic stock solution of the compound tested or 100 μl of absolute ethanol (blank). Each compound is tested at a final concentration of 20 μM. The reaction medium is equilibrated for 2 minutes at 37° C. Then 50 μl of 6.6 mM tert-butyl hydroperoxide (t-BuOOH) in ultrapure water, or 3.3 mM hydrogen peroxide (H$_2$O$_2$) in ultrapure water are added. The glutathione peroxidase activity is determined at 37° C. by measuring the decrease of absorbance at 340 nm for 5 minutes. Said activity or initial enzymatic rate is proportional to the slope of the variation of absorbance with time.

The catalytic activity of oxygen reduction of the compounds tested corresponds to the rate of consum.p.ion of NADPH in the absence of hydroperoxide. When this rate is significantly greater than that of the control, the corresponding glutathione oxidase activity can be checked by the direct measurement of the kinetics of consum.p.ion of the dissolved oxygen with the aid of a Clark electrode.

The results of glutathione peroxidase activity measurements are shown in Table 1 below. They are expressed in nmoles of hydroperoxide reduced per minute.

TABLE 1

Glutathione peroxidase activity
(in nmoles of hydroperoxide reduced/min)
pH = 7.3; 37° C.; [GSH] = 2 mM

|  | t-BuOOH | $H_2O_2$ |
| --- | --- | --- |
| BXT-51097 | 11.4 | 39.8 |
| BXT-51100 | 10.1 | 37.1 |
| BXT-51103 | 15.5 | 34.9 |
| BXT-51105 | 13.9 | 35.7 |

As shown in Table 1 the compounds of general structure I described in the present invention catalyze, in the presence of glutathione GSH, the reduction of hydrogen peroxide or that of an organic hydroperoxide.

EXAMPLE 6
Inhibition of the TNF-α-Induced Release of Interleukin 8 by Endothelial Cells It is well known to the person skilled in the art that the release of interleukin 8 (IL8) causes a massive accumulation of activated neutrophils and thus participates in the inflammatory process and/or tissue degradation process (see Baggiolini M. et al.; FEBS Letters, 307, 1, 97–101, 1992).

Human endothelial cells are grown at 37° C. in multi-well plates under a water-saturated atmosphere constituted of a gaseous mixture of 95% air and 5% $CO_2$. Their culture medium is constituted by a medium M 199 pH=7.4 containing 20% foetal calf serum, 2 mM L-glutamine, 100 U/ml penicillin, 100 μg/ml streptomycin and 1% by volume of a medium supplement containing heparin and a growth factor for these cells.

When the cells are close to confluence, they are incubated for one hour in the presence or in the absence of one of the following compounds: BXT-51097 or BXT-51103. Each one of these compounds is incorporated at 10 μM in the culture medium containing 2% foetal calf serum, everything else being equal. After removal of the culture medium, the cells are incubated in the presence or in the absence (control) of TNF-α, at 1 ng/ml, in the same culture medium as before. In the case of cells pre-treated with a compound of the invention, the medium further contains the same compound at 10 μM. After three hours and thirty minutes of incubation, the interleukin 8 (IL-8) released into the culture medium is determined by ELISA.

The results obtained are given in the annexed FIG. 1. These results show that the incubation of the endothelial cells in the presence of TNF-α leads to an increase in the production of IL-8 in the culture medium, and that the treatment of the cells by the compounds BXT-51097 and BXT-51103 inhibits this effect by at least 85%.

These results demonstrate that such compounds can act as TNF-α antagonists in terms of interleukin 8 release by endothelial cells.

EXAMPLE 7
Inhibition of TNF-α-Induced P- and E-Selectin Expressions by Endothelial Cells It has been shown that the initial phase of inflammation is mediated by adhesion molecules of the E- and/or P-selectin type (see ALBELDA S. M. et al., FASEB Journal, 8, 504–512, 1994).

Human endothelial cells are grown under the same conditions as those described in Example 6.

When the cells are close to confluence, they are incubated for one hour in the presence or in the absence of one of the following compounds: BXT-51097 or BXT-51103. Each one of these compounds is incorporated at 10 μM in the culture medium containing 2% foetal calf serum, everything else being equal. After the removal of the culture medium, the cells are incubated in the presence or in the absence (control) of TNF-α, at 1 ng/ml, in the same culture medium as before. In the case of cells pre-treated with a compound, the medium further contains the same compound at 10 μM. After three hours and thirty minutes of incubation, the cells are washed with PBS buffer and they are fixed with 2% formaldehyde in the same buffer. The P- and E-selectin expressions on the cells are then measured by an ELISA determination by successively incubating the cells in the presence of a mouse monoclonal antibody, anti-P-selectin and anti-E-selectin respectively, and a rabbit anti-mouse anti-antibody labelled with alkaline phosphatase. The quantification is carried out upon the addition of para-nitrophenyl phosphate whose hydrolysis is followed at 405 nm.

Figure 2:
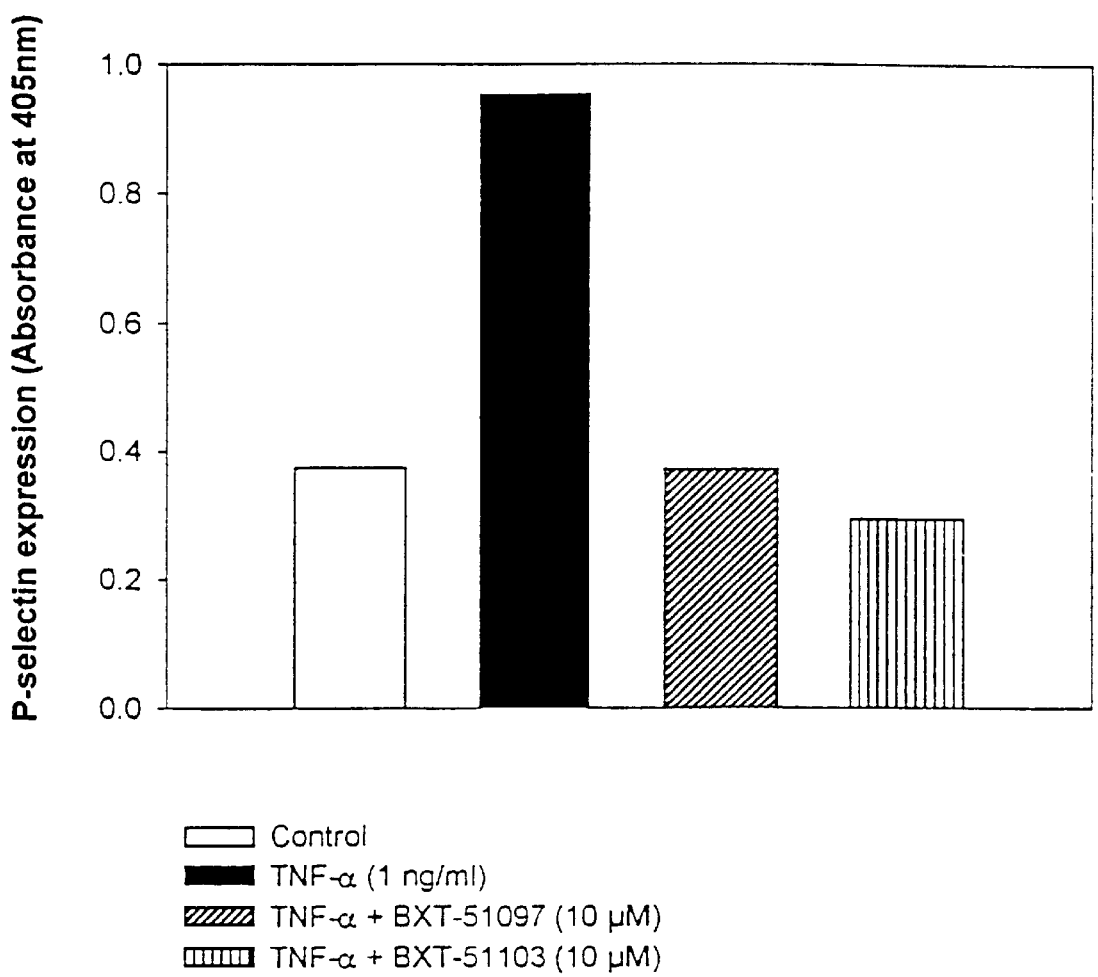
FIG. 2 shows the inhibition of the TNF-α-induced P-selectin expression by endothelial cells (HUVEC).
Figure 3:
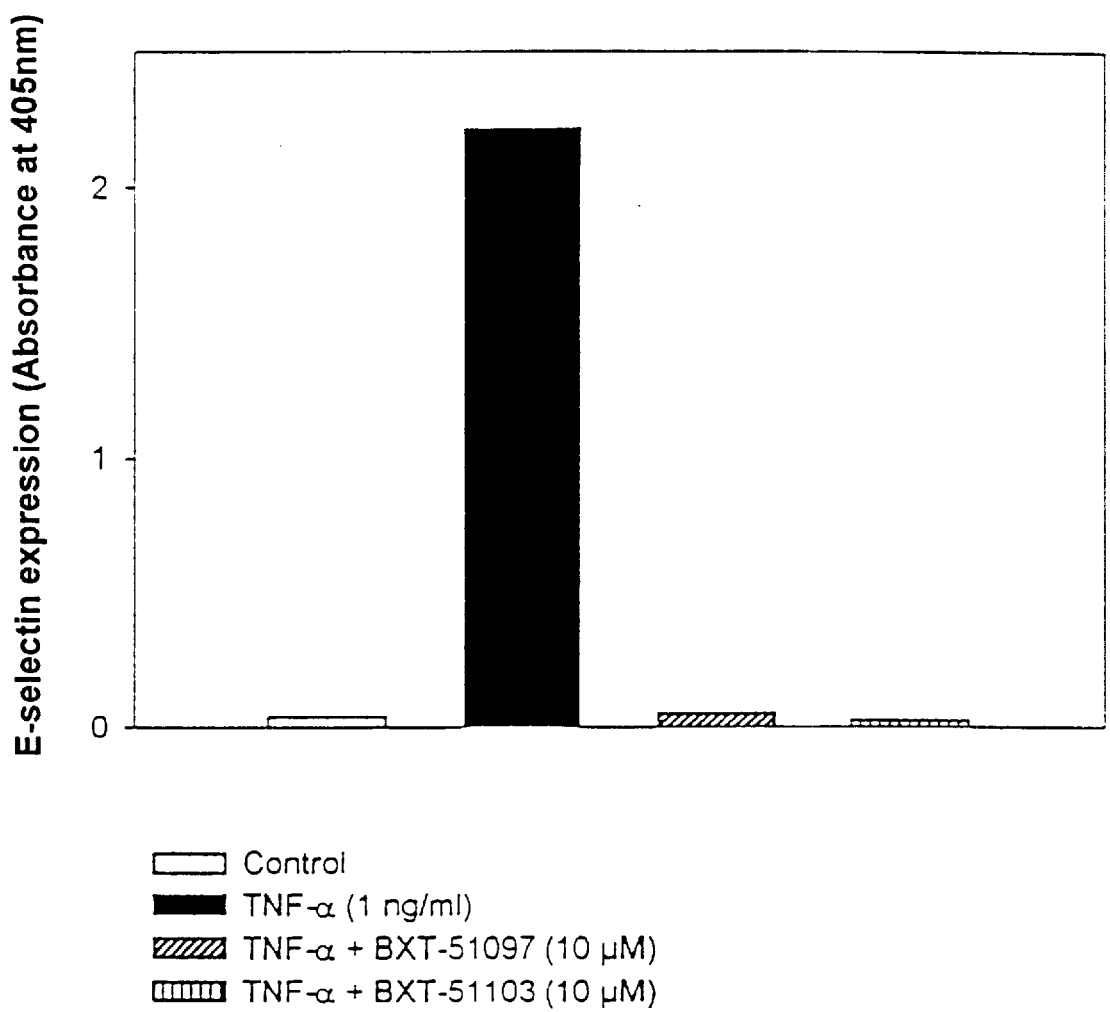
FIG. 3 shows the inhibition of the TNF-α-induced E-selectin expression by endothelial cells (HUVEC).

The results obtained corresponding to the measurements of P- and E-selectin expressions are shown in the annexed FIGS. 2 and 3 respectively. These results show that the incubation of endothelial cells in the presence of TNF-α induces the expression of P- and E-selectin, which is in both cases totally inhibited when the cells are treated with the compounds BXT-51097 and BXT-51103.

The results show that such compounds are capable of inhibiting the TNF-α-induced expression of cell adhesion molecules such as P- and E-selectin.

The whole of these results show that the compounds of the invention having formula I:

1/catalyse the reduction of hydroperoxides in the presence of glutathione;

2/antagonize the action of TNF-α;

3/inhibit the expression of cell adhesion molecules.

TNF-α, as well as the expression of adhesion molecules such as P- and E-selectins, having been implicated in pathologies which involved an over-production of hydroperoxides, the molecules of the present invention of the general formula I therefore constitute valuable active principles and, after formulation, powerful drugs enabling the treatment of the corresponding pathologies.

What is claimed is:

1. A cyclic organoselenium compound of the general formula (I):

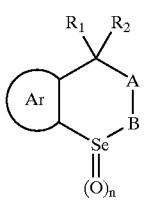

(I)

in which:

$R_1$=hydrogen; lower alkyl; optionally substituted aryl; optionally substituted lower aralkyl;

R₂=hydrogen; lower alkyl; optionally substituted aryl; optionally substituted lower aralkyl;

A=CO; (CR₃R₄)ₘ;

B=NR₅;

Ar=an optionally substituted radical of formula:

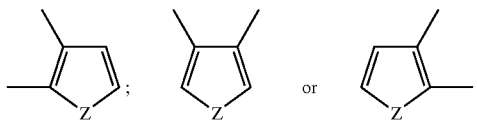

in which:

Z=O; S ; NR₅;

R₃=hydrogen; lower alkyl; optionally substituted aryl; optionally substituted lower aralkyl;

R₄=hydrogen; lower alkyl; optionally substituted aryl; optionally substituted lower aralkyl;

R₅=hydrogen; lower alkyl; optionally substituted aryl; optionally substituted lower aralkyl; optionally substituted heteroaryl; optionally substituted lower heteroaralkyl; CO(lower alkyl); CO(aryl); SO₂(lower alkyl); SO₂(aryl);

m=0 or 1;

n=0 or 1;

or a pharmaceutically acceptable salt of acids and bases.

2. A cyclic organoselenium compound of the general formula (I), according to claim 1, selected from the group consisting of:

4,4-dimethyl-thieno-[3,2-e]-isoselenazine, 4,4-dimethyl-thieno-[3,2-e]-isoselenazine-1-oxide, 4,4-dimethyl-thieno-[2,3-e]-isoselenazine, and 4,4-dimethyl-thieno-[2,3-e]-isoselenazine-1-oxide.

3. A method of preparation of cyclic organoselenium compounds, of the general formula (I), according to claim 1, characterized in that it comprises the following steps:

a/preparing or using an orthohalo(Ar)acetonitrile compound or a orthohalo(Ar)acetonitrile compound mono- or gem- disubstituted in the benzylic position;

then:

for the preparation of said compounds of formula (I) in which A=(CR₃R₄)ₘ with m=0 and n=0:

b1/hydrolyzing said nitrile compound into an amide compound, c1-1/transforming this into an amine compound by a transposition reaction according to conventional methods, d1-1/allowing said amine compound to react with a nucleophilic selenium compound in the presence of a copper Cu(I) salt, in a polar organic solvent, to lead to the corresponding (Ar)isoselenazoline compound; or for the preparation of said compounds of formula (I) in which A=CO and n=0:

b1/hydrolyzing said nitrile compound into an amide compound, c1-2/allowing said amide compound to react with a nucleophilic selenium compound in the presence of a copper Cu(I) salt, in a polar organic solvent, to lead to the corresponding (Ar)iso-selenazone compound; or for the preparation of said compounds of formula (I) in which A=CH₂ and n=0:

b2/reducing said nitrile compound into an amine compound, c2/allowing said amine compound to react with a nucleophilic selenium compound in the presence of a copper Cu(I) salt, in a polar organic solvent, to lead to the corresponding (Ar)isoselenazine compound; or for the preparation of said compounds of formula (I) in which A=(CR₃R₄), A being other than CH₂ and n=0:

b3/carrying out a mono- or a bis-C-alkylation of said nitrile compound according to conventional methods; and c3/allowing the amine compound obtained to react with a nucleophilic selenium compound in the presence of a copper Cu(I) salt, in a polar organic solvent, to lead to the corresponding (Ar) isoselenazine compound.

4. The method of claim 3 wherein the compound resulting from step d1-1, step c1-2, step c2 or step c3 is further reacted by N-alkylating, N-arylating, N-acylating or N-sulphonylating, according to conventional procedures, said corresponding (Ar)isoselenazine compound.

5. The method of claim 3 wherein, for the preparation of compounds of formula (I) in which n=1, Se-oxidising, according to conventional procedures, the corresponding compound of formula (I) wherein n=0.

6. The method of claim 3 wherein said reducing said nitrile compound into an amine compound is performed with the aid of borane in tetrahydrofuran.

7. The method of claim 3 wherein said carrying out a mono- or a bis-C-alkylation of said nitrile compound according to conventional methods is performed with the aid of an organolithium compound in tetrahydrofuran.

8. The method of claim 3 wherein said selenium compound is generated in situ.

9. A pharmaceutical composition comprising at least one compound of general formula (I) of claim 1, or a pharmaceutically acceptable acid or base salt thereof, and a pharmaceutically acceptable excipient, carrier or vehicle.

10. The pharmaceutical composition of claim 9 comprising said compound in an amount of between about 0.1% and about 5% by weight.

11. The pharmaceutical composition according to claim 10 comprising said compound in an amount between about 0.1% and about 1% by weight.

12. The pharmaceutical composition according to claim 9 comprising from about 1 to about 500 mg of at least one compound of general formula (I).

13. A pharmaceutical composition comprising a cyclic organoselenium compound of claim 2 or a pharmaceutically acceptable acid or base salt thereof, and a pharmaceutically acceptable excipient, carrier or vehicle.

14. A method of treatment of a patient suffering from a functional impairment of cells or tissues related to an over-production of cytotoxic hydroperoxides, comprising administering to said patient an effective amount of at least one compound of formula (I) of claim 1.

15. The method of claim 14 wherein said impairment is selected from the group consisting of inflammatory cardiovascular pathologies; inflammatory cerebrovascular pathologies; ischemic cardiovascular pathologies; ischemic cerebrovascular pathologies; inflammatory digestive pathologies; ischemic digestive pathologies; inflammatory respiratory pathologies; ischemic respiratory pathologies; inflammatory ophthalmic pathologies; ischemic ophthalmic pathologies; cataracts; acute ophthalmic allergies; impairments of the retina which are associated with macular degeneration; viral infections causing an immunodeficiency; and post-radiotherapy fibroses.

16. The method of claim 15 wherein said inflammatory digestive pathology or ischemic digestive pathology is inflammation of the bowel.

17. The method of claim 16 wherein said inflammation of the bowel is Crohn's disease or hemorrhagic rectocolitis.

18. The method of claim 15 wherein said inflammatory respiratory pathology or ischemic respiratory pathology is adult respiratory distress syndrome or infant respiratory distress syndrome.

19. The method of claim 15 wherein said inflammatory ophthalmic pathology or ischemic ophthalmic pathology is glaucoma.

20. The method of claim 15 wherein said viral infection causing an immunodeficiency is AIDS.

21. The method of claim 15 wherein said ischemic cardiovascular or ischemic cerebrovascular pathologies comprises arterial restenoses following an angioplasty, arterial stenoses following artery allografts, intermittent claudication in patients affected with obstructive ischemia of the lower members, or cerebrovascular accidents of ischemic origin.

22. The method of claim 14 wherein said over-production of cytotoxic hydroperoxide is due to activation of intracellular metabolic pathways; activation of enzymes contained in endothelial cells or in blood platelets; activation by cytokines of inflammatory cells, activation by cytokines of immune cells; intoxication by a free-radical generating xenobiotic; voluntary irradiation, or accidental irradiation.

23. The method of claim 22 wherein said intracellular metabolic pathways are selected from the group consisting of flavine oxygenases, lipoxygenases, monoamine oxidases, and cytochrome P-450 oxygenases.

24. The method of claim 22 wherein said enzyme contained in endothelial cells is selected from xanthine oxidase and 15-lipoxygenase.

25. The method of claim 22 wherein said enzymes in blood platelets is selected from the group consisting of cyclooxygenase and 12-lipoxygenase.

26. The method of claim 22 wherein said cytokine is TNF-$\alpha$.

27. The method of claim 22 wherein said inflammatory or immune cells are selected from the group consisting of neutrophils, macrophages and lymphocytes.

28. A method of treatment of a patient suffering from a functional impairment of cells or tissues related to an over-production of cytotoxic hydroperoxides, comprising administering to said patient an effective amount of at least one compound of claim 2.

* * * * *